(12) United States Patent
Marsman

(10) Patent No.: US 10,799,686 B2
(45) Date of Patent: Oct. 13, 2020

(54) GUIDEWIRE TORQUER

(71) Applicant: Johan Willem Pieter Marsman, Hilversum (NL)

(72) Inventor: Johan Willem Pieter Marsman, Hilversum (NL)

(73) Assignee: Johan Willem Pieter Marsman, Hilversum (NL)

( * ) Notice: Subject to any disclaimer, the term of this patent is extended or adjusted under 35 U.S.C. 154(b) by 349 days.

(21) Appl. No.: 15/692,054

(22) Filed: Aug. 31, 2017

(65) Prior Publication Data

US 2018/0050178 A1    Feb. 22, 2018

Related U.S. Application Data

(63) Continuation-in-part of application No. 15/266,805, filed on Sep. 15, 2016, now abandoned, and a continuation-in-part of application No. PCT/NL2016/050281, filed on Apr. 21, 2016.

(51) Int. Cl.
*A61B 5/00* (2006.01)
*A61M 25/09* (2006.01)

(52) U.S. Cl.
CPC .......... *A61M 25/09041* (2013.01); *A61M 2025/0915* (2013.01); *A61M 2025/09116* (2013.01); *A61M 2205/0216* (2013.01); *A61M 2205/0266* (2013.01); *A61M 2205/582* (2013.01); *A61M 2205/583* (2013.01)

(58) Field of Classification Search
CPC .. A61M 25/09041; A61M 2025/09116; A61M 25/09; A61M 2025/0915; A61M 2205/0216; A61M 2205/0266; A61M 2205/582; A61M 2205/583
See application file for complete search history.

(56) References Cited

U.S. PATENT DOCUMENTS

| | | | |
|---|---|---|---|
| 8,968,214 B2* | 3/2015 | Numata | A61M 25/002 600/585 |
| 9,050,439 B1* | 6/2015 | Mauch | A61M 25/09 |
| 9,351,735 B2* | 5/2016 | Nagano | A61M 25/09041 |
| 10,675,448 B2* | 6/2020 | Whittaker | A61M 25/09041 |
| 2005/0096566 A1* | 5/2005 | Arnott | A61M 25/09041 600/585 |

(Continued)

*Primary Examiner* — Max F Hindenburg
(74) *Attorney, Agent, or Firm* — Leydig, Voit & Mayer, Ltd.

(57) ABSTRACT

A guidewire torquer comprising a handling body for handling of the guidewire torquer and guidewire holding surfaces oriented for engaging the guidewire from mutually opposite sides of the guidewire and holding the guidewire in an elastically tensioned, bent guidewire shape providing frictional fixation of the guidewire relative to the handling body. The guidewire holding surfaces project from an abutment plane defined by at least one abutment surface. A guidewire trajectory of the bent guidewire shape extends along and touches the guidewire holding surfaces is accessible from a direction in which the at least one abutment surface is facing. At least portions of the guidewire holding surfaces lean over towards or face the abutment plane for holding the guidewire adjacent to said abutment plane, and the guidewire holding surfaces are part of a single, rigid body portion.

14 Claims, 5 Drawing Sheets

(56) References Cited

U.S. PATENT DOCUMENTS

| | | | | |
|---|---|---|---|---|
| 2010/0010475 A1* | 1/2010 | Teirstein | ............... | A61M 25/02 |
| | | | | 604/528 |
| 2012/0216385 A1* | 8/2012 | Taylor | ................... | A61M 25/02 |
| | | | | 29/428 |
| 2013/0190731 A1* | 7/2013 | Cude | ............... | A61M 25/09041 |
| | | | | 604/528 |
| 2014/0276441 A1* | 9/2014 | Cohen | ................... | A61M 25/02 |
| | | | | 604/180 |
| 2015/0105650 A1* | 4/2015 | Burkett | ............... | A61B 1/3137 |
| | | | | 600/407 |

\* cited by examiner

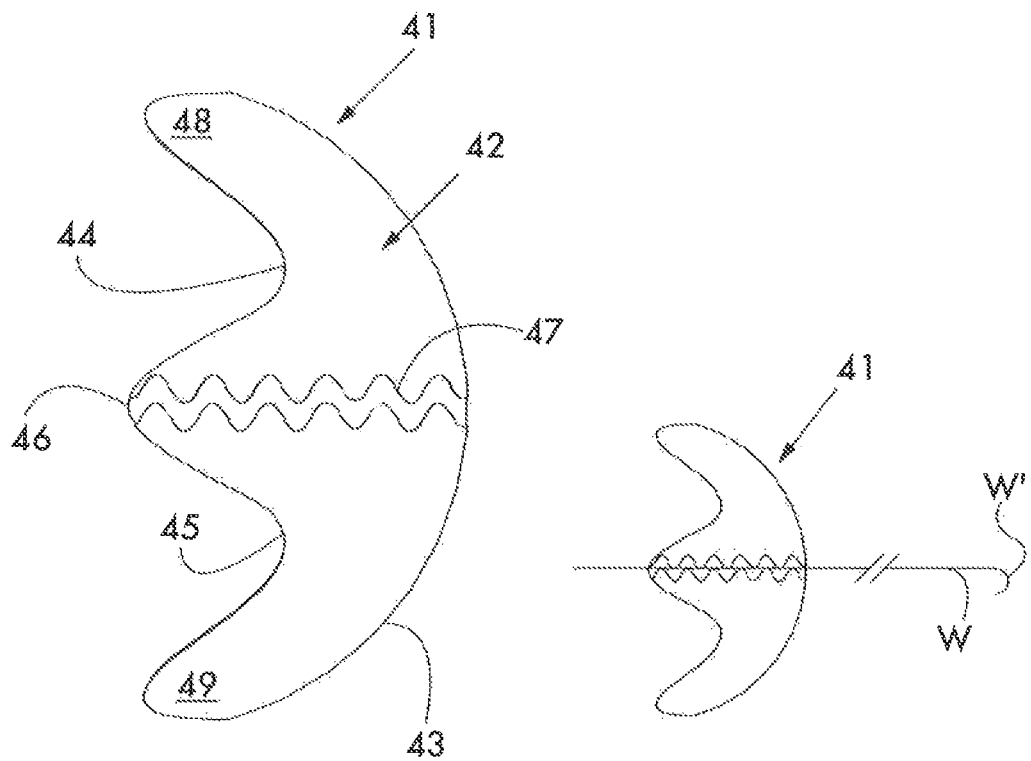
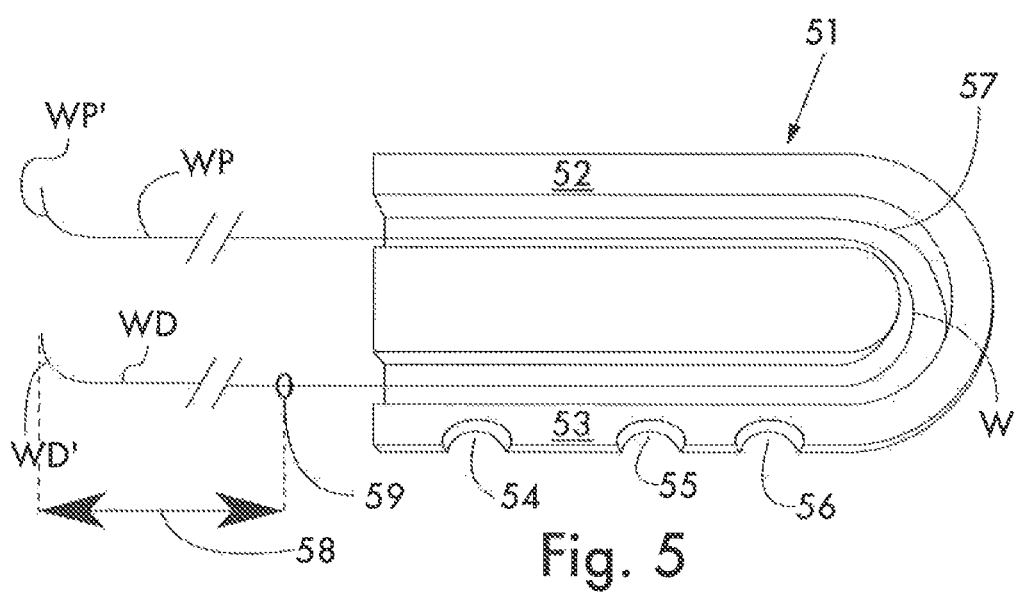

GUIDEWIRE TORQUER

CROSS-REFERENCE TO RELATED APPLICATIONS

This application claims priority to U.S. application Ser. No. 15/266,805, filed Sep. 15, 2016, which claims priority to International Application No. PCT/NL2016/050281, filed Apr. 21, 2016, both of which are expressly incorporated by reference in their entirety, including the contents of any references contained therein.

FIELD OF THE INVENTION

The present invention relates to a guidewire torquer.

BACKGROUND OF THE INVENTION

A guidewire torquer is a device that is used in a number of different medical procedures to guide vascular catheters, catheter-mounted heart valves, aortic endografts, endotracheal tubes, or gastric feeding tubes and the like into a patient towards a desired location within the patient. Guidewires are used in a number of diagnostic and interventional fields, such as diagnostic and interventional cardiology, diagnostic and interventional neuroradiology, diagnostic and interventional radiology, urology, gastroenterology, vascular surgery, minimally invasive vascular interventions such as angioplasty, stenting, thrombolysis, transcatheter aortic valve insertion (TAVI), and endovascular abdominal aortic aneurysm repair (EVAR).

In vascular uses, a physician is required to navigate the guidewire through the vasculature of the patient. This is done in order to position the distal end of the guidewire at a desired location. Then a diagnostic or therapeutic catheter is fed over the guidewire to the desired location for the planned vascular intervention. In the text, the distal end of the guidewire is the end that is to enter the human body. The proximal end of the guidewire is in the hands of the physician and is not inserted into the body.

In other uses, a physician is required to navigate the guidewire through hollow organs, such as the urinary tract, the gastro-intestinal tract, and the bile ducts. This is done in order to position the distal end of the guidewire at a desired location. Then a diagnostic or therapeutic catheter is fed over the guidewire to the desired location for the planned intervention (e.g. dilating or stenting a narrowed duct).

The distal end of the guidewire generally has a tip adjusted to help steering the guidewire, such as an angled tip or a tip shaped like a J. Positioning the distal end of the guidewire at the desired location can be tough and time consuming due to complex vascular anatomy and due to abnormalities of the vessel lumen caused by vascular disease. The physician manipulates the distal end of the guidewire through the vasculature of the patient to the desired location by pinching and torqueing the proximal end of the guidewire with his fingers.

Guidewires are relatively fine and difficult to grip between the physician's fingers, thereby making the positioning of the guidewire challenging. Handling of the guidewire is hampered by the fact that the guidewire is often slippery particularly when wetted with saline or blood. A guidewire is also intended to be smooth by means of various kinds of coating in order to provide lubricity between the guidewire surface and the inner surface of the vessel wall.

Due to the slipperiness of the guidewire the physician cannot accurately and securely rotate or move the guidewire lengthwise in and out of the body. It is also difficult to reliably feel with his fingers to what extent the guidewire follows his steering manipulations. As such, a device called a guidewire torque device, guidewire torquer, or steering handle, is often affixed to the guidewire in order to allow the physician to better grip and impart motion to the guidewire. That is, the guidewire torquer device is intended to allow the physician to securely control the movements of the guidewire and to steer the distal end of the guidewire by rotational and longitudinal manipulation of the guidewire.

One disadvantage of prior art guidewire torquers is that they are configured to be attached from and over the proximal end of a guidewire. Generally, guidewire torquers must be back loaded over the proximal end of the guidewire, and then advanced along the guidewire until a suitable location is reached. After that a reliable fixation between guidewire and torquer is required, which may be unreliable or damage the guidewire by kinking or breakage or detachment of surface particles, in many applications, the torquer is brought into engagement with the guidewire close to the point of entry into the patient's body to obtain a control over the guidewire tip advancement and orientation approximately about the guidewire axis that is as direct as possible. However, once a difficult section has been crossed, the torquer needs to be disengaged from the guidewire to allow further advancement of the guidewire during which the section of the guidewire to which the torquer was engaged passes into the patient. In such applications, damage to the guidewire usually means that the guidewire must be retracted and replaced by a new one, because inserting a damaged guidewire section into the patient would result in an unacceptable risk of complications.

Furthermore, prior art guidewire torquers are complex, consisting of multiple moving parts, and therefore are relatively expensive.

SUMMARY OF THE DISCLOSURE

In order to improve such prior art, the present invention provides, in a first embodiment, a guidewire torquer for manually controlling a guidewire and imparting motion to a guidewire, the guidewire torquer including:
  a handling body for handling of the guidewire torquer, and
  guidewire holding surfaces oriented bar engaging the guidewire from mutually opposite sides of the guidewire and holding the guidewire in an elastically tensioned, bent guidewire shape providing frictional fixation of the guidewire relative to the handling body,
  the guidewire holding surfaces projecting from at least one abutment plane defined by at least one abutment surface,
  a guidewire trajectory of the bent guidewire shape extending along and touching the guidewire holding surfaces being accessible from a direction in which the at least one abutment surface is facing.
  at least portions of the guidewire holding surfaces leaning over towards or face the abutment plane for holding the guidewire adjacent to the abutment plane, and
  the guidewire holding surfaces being part of a single, rigid body portion.
In a further embodiment, the present invention provides a kit comprising:
  a guidewire, and
  a guidewire torquer for manually controlling a guidewire and imparting motion to a guidewire, the guidewire torquer including:
  a handling body for handling of the guidewire torquer, and guidewire holding surfaces oriented for engaging the guidewire from mutually opposite sides of the guidewire and holding the guidewire in an elastically tensioned, bent guidewire shape providing frictional fixation of the guidewire relative to the handling body, wherein the guidewire holding surfaces project from at least one abutment surface defining a plane against which the guidewire abuts when held in the elastically tensioned, bent guidewire shape, and wherein a guidewire trajectory of the bent guidewire shape along and touching the guidewire holding surfaces is accessible from a direction in which the at least one abutment surface is facing, wherein at least portions of the guidewire holding surfaces lean over towards or face the at least one abutment surface for holding the guidewire adjacent to the at least one abutment surface, and wherein the guidewire holding surfaces are part of a single, rigid body portion.

In another embodiment, the present invention provides a method of inserting a guidewire into a patient, the method comprising:

providing a guidewire;

providing a guidewire torquer having a handling body and guidewire holding surfaces facing in generally opposite directions;

inserting a distal portion of the guidewire, via an opening made in a patient, into a duct of the patient;

prior to or after the insertion, positioning a section of the guidewire in an elastically tensioned, bent guidewire shape engaged by the guidewire holding surfaces by displacement relative to the torquer in a direction generally lateral to the section of the guidewire, the guidewire holding surfaces engaging the guidewire from mutually opposite sides of the guidewire and providing frictional fixation of the guidewire relative to the handling body;

after the insertion, holding the handling body of the guidewire torquer so that a torque is exerted onto the guidewire;

causing the guidewire torquer to be disengaged from the section of the guidewire by displacement of the guidewire section relative to the guidewire torquer in a direction generally lateral to the section of the guidewire; and subsequently further inserting the guidewire into the patient, wherein the section previously engaged by the guidewire torquer passes through the opening into the duct, until a distal tip of the guidewire has reached a predetermined end position inside the patient.

In a particular embodiment, the present invention provides a guidewire torquer for manually controlling a guidewire and imparting motion to a guidewire, the guidewire torquer comprising:

a handling body for handling of the guidewire torquer, and an insertion channel for receiving the guidewire, the insertion channel being arranged at a surface of the handling body, wherein the handling body comprises a shaping feature, which shaping feature provides visible and/or tactile feedback as to the orientation of the guidewire, wherein the insertion channel provides a frictional fixation of the guidewire relative to the handling body, wherein the insertion channel is accessible in a direction transverse to the insertion channel over the whole length thereof, and wherein the insertion channel has at least one bend.

In a further particular embodiment, the present invention provides a kit comprising:

a guidewire, and a guidewire torquer for manually controlling a guidewire and imparting motion to a guidewire, the guidewire torquer comprising:

a handling body for handling of the guidewire torquer, and an insertion channel for receiving the guidewire, the insertion channel being arranged at a surface of the handling body, wherein the handling body comprises a shaping feature, which shaping feature provides visible and/or tactile feedback as to the orientation of the guidewire, wherein the insertion channel provides a frictional fixation of the guidewire relative to the handling body, wherein the guidewire has an insertion tip with a curvature for inserting into the human body, and wherein the guidewire further has an indicator tip at an end of the guidewire opposite of the insertion tip, and wherein, if between the insertion tip and the indicator tip, the guidewire is in a straight condition:

the insertion tip and the indicator tip are curved to a common side of the guidewire for indicating the direction of the insertion tip as depending from the direction of the indicator tip, or the insertion tip and the indicator tip are curved to mutually opposite sides of the guidewire, for indicating the direction of the insertion tip as depending from the direction of the indicator tip if the guidewire is bent into a U-shaped or V-shaped configuration.

After insertion of the guidewire into the patient and before disengaging the guidewire torquer from the section of the guidewire that was engaged thereby, the handling body of the guidewire torquer may be moved towards the opening in the patient so that the guidewire is further inserted into the patient, e.g. until the guidewire torquer has reached a position close to the opening made in the patient.

Subsequently, a more proximal section of the guidewire may be brought in engagement with the guidewire torquer, which may again be moved towards the opening in the patient so that the guidewire is inserted further into the patient, e.g. until a distal tip of the guidewire has reached a predetermined end position inside the patient or the step of disengaging the guidewire torquer from the guidewire and re-engaging the guidewire torquer to a more proximal section of the guidewire may again be repeated.

After the guidewire torquer has been brought in engagement with the guidewire, the guidewire torquer may be placed horizontally on a substantially flat surface in such a position that the rotational orientation of the distal portion of the guidewire remains pointing into the predetermined direction while, subsequently, a next section of the guidewire is inserted into the patient, via the opening in the patient and the guidewire torquer slides over the substantially flat surface and the rotational orientation of the distal portion of the guidewire tip remains pointing into the predetermined direction.

The guidewire holding surfaces facing in generally opposite directions may for instance be arranged for holding the guidewire in a Substantially U-shaped or V-shaped configuration, so that visible feedback concerning the insertion depth of the distal end of the guidewire into the patient relative to the opening in the patient is provided by the position of the proximal tip end of the guidewire relative to the opening in the patient.

A main advantage of the invention is that a superior and reliable manual control of the guidewire can be provided while the mounting of the guidewire torquer to the guidewire and the disengagement of the guidewire torquer from the guidewire can be performed in a simple manner.

Also, the mounting of the guidewire torquer to the guidewire can be performed at any spot of the guidewire as seen lengthwise to the guidewire, without the need for back loading the guidewire torquer over the proximal end of the guidewire.

Because of the frictional fixation of the guidewire by normal forces induced by bending loads exerted by the torquer onto the guidewire section inside the guidewire torquer, forces exerted by the guidewire torquer on the guidewire are spread over the contact area of frictional fixation and the fixation is highly reliable. Also, no movable parts are required to provide such friction.

Due to the fact, that forces exerted by the guidewire torquer on the guidewire are spread over the contact area, the following known problem of the prior art is prevented. In prior art devices clamping elements such as screws or claws pose a risk of detachment of particles from the coating of the guidewire, which is especially so in case of slippage of the guidewire relative to the torquer. Such damage, also known as local stripping of surface material or coating from the guidewire may pose health risks to patients being operated on, when such particles are entrained into the human body.

Another aspect of possible damage by prior art devices to the guidewire is that a point force exerted by the guidewire torquer leads to deformation of the contour and shape of the guidewire, which could even lead to kinking or breakage of the wire. Such damages are prevented with the present guidewire torquer.

Also, the presented guidewire torquer provides a very direct tactile and visible feedback to the physician concerning the rotational orientation of the guidewire and in particular concerning the rotational orientation of the distal tip of the guidewire inside the body of the patient.

Since the guidewire holding surfaces are part of a single, rigid body portion, the guidewire can be inserted easily and is rigidly fixed against rotation relative to the torquer. Exerting a torque to the guidewire results in very little or no rotation of the guidewire relative to the guidewire torquer where the guidewire is engaged by the torquer.

BRIEF DESCRIPTION OF THE DRAWINGS

While the appended claims set forth the features of the present invention with particularity, further advantages, features and details of the present invention will be elucidated on the basis of a description of one or more embodiments with reference to the accompanying figures, of which:

FIGS. 4A and 4B provide two front views of a further preferred embodiment according to the present invention;

FIG. 5 provides a perspective view of a further preferred embodiment according to the present invention;

DETAILED DESCRIPTION OF THE DRAWINGS

Figure 1:
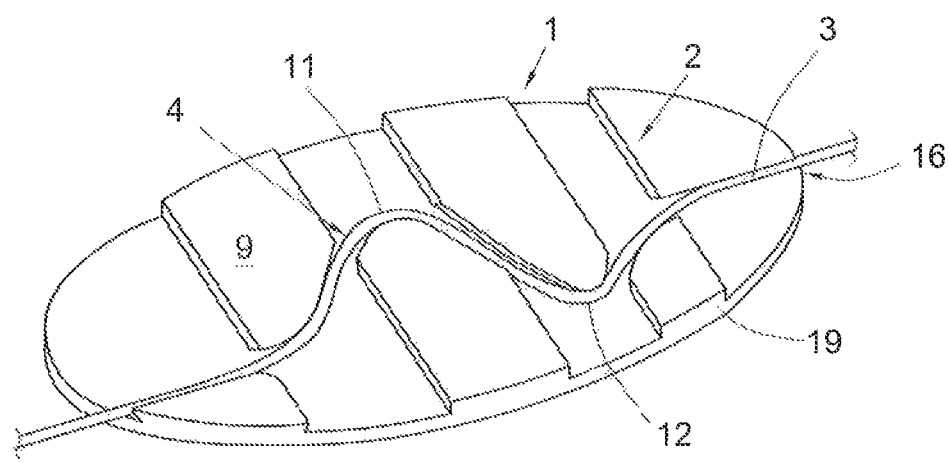
FIG. 1 provides a perspective view of a first preferred embodiment according to the present invention.
Figure 2A:
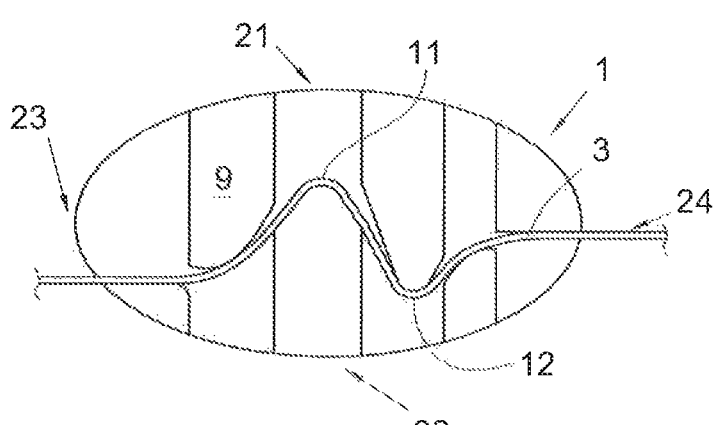
FIGS. 2A, 2B, 2C and 2D provide four further views of the embodiment of FIG. 1.
Figure 2B:
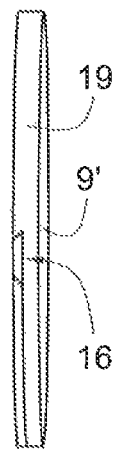

FIG. 1 shows a perspective view of a guidewire torquer 1 according to a first preferred embodiment according to the invention. FIGS. 2A-2D show further views of the guidewire torquer 1. FIGS. 1 and 2A show the guidewire torquer 1 holding a guidewire 3. The guidewire 3 is elastically tensioned by the guidewire torquer 1 into a bent guidewire shape. The guidewire torquer 1 is comprised of a single handling body 2, which may for instance be (injection) molded, machined or manufactured using an additive process such as 3D-printing. The forming of the guidewire torquer from a single part provides a low complexity and expense of the device. The guidewire torquer 1 has the shape of a substantially flat, oval disc. The longitudinal diameter of the oval disc is about twice as long as the transverse diameter of the oval disc. The guidewire torquer 1 includes a front surface 9, a back surface 9', a top side 21, and a bottom side 22, a left side 23, a right side 24 and a circumference surface 19.

A guidewire trajectory or insertion channel 16 in the handling body 2 has a plurality of guidewire holding surfaces 7, 8 oriented for engaging the guidewire 3 from mutually opposite sides of the guidewire and holding the guidewire in an elastically tensioned, bent guidewire shape providing frictional fixation of the guidewire relative to the handling body 2. The guidewire holding surfaces 7, 8 project from an abutment plane defined by an abutment surface 5. The guidewire trajectory 16 is accessible from a direction in which the abutment surface 5 is facing.

The guidewire trajectory 16 comprises a curved section 4 having a top bend 11 and a bottom bend 12. The guidewire 3 is forced to follow the bends imposed by the guidewire, holding surfaces 7, 8 resulting in normal forces and accordingly friction between the guidewire and the guidewire holding surfaces. Because of the friction and the rigid construction of the handling body 2, the guidewire 3 is firmly fixed relative to the handling body.

The guidewire holding surfaces 7, 8 lean over towards the abutment plane 5 for holding the guidewire adjacent to the abutment plane as a result of the tendency of the guidewire 3 to elastically flex back to its original straight shape. The guidewire holding surfaces 7, 8 are part of a single, rigid body portion 2.

The rigid body portion 2 holding the guidewire constitutes a particularly stiff engagement of the guidewire, so that steering can be carried out with great precision and a very direct feel. For this effect, it is particularly advantageous if the handling body 2 is of a material having a modulus of elasticity (Young's tensile at 20° C.) of at least 0.5 GPa and preferably at least 1.0 GPa or at least 1.5 GPa and/or it has a material thickness at the abutment surface of at least 2 mm and preferably at least 3 mm. The handling body may for instance be made from a rigid polymer material, such as PET, PLA, ABS, PMMA, POM or PA.

For a direct steering feeling and for low manufacturing costs, it is advantageous that the guidewire torquer 1 is made of one part. Because the guidewire torquer is free of handling body portions opposite of each of the guidewire holding surfaces, room is left for slides of a mold defining the overhanging guidewire holding surfaces. If openings are provided in the abutment surface directly adjacent to the overhanging guidewire holding surfaces, the overhanging guidewire holding surfaces may be formed by mold portions projecting through these openings in mold opening direction after the handling body has been molded. When manufacturing is carried out by 3D printing, non-releasing shapes, such as overhanging guidewire holding surfaces can be made particularly easily.

For holding the guidewire with sufficient pre-tension to allow a large torque to be exerted, the guidewire holding surfaces are preferably arranged such that, in a view of said bent guidewire shape perpendicular to a plane in whish the guidewire is curved, the amplitude of a succession of bends is more than 0.1 and preferably more than 0.2 times the distance between successive peaks or successive deepest positions of valleys in the succession of bends. Also, for exerting a large torque it can be provided that at least portions of the guidewire holding surfaces have a higher coefficient of friction relative to a guidewire than other surface portions of the torquer.

For allowing a large torque to be exerted, without having to bend the guidewire beyond its maximum elastic deformability, it is furthermore advantageous if the guidewire holding surfaces are arranged such that, in a view of said bent guidewire shape perpendicular to a plane in which the guidewire is curved, the amplitude and number of bends is geared to the maximum elastic deformability of the materials the guidewire is made of. Generally, for Nitinol guidewires having a higher maximum elastic deformability than stainless steel guidewires a guidewire torquer that constitutes one high peak and one low valley, as in the present example, will result in a sufficiently large torque. For stainless steel guidewires having a lower maximum elastic deformability than Nitinol guidewires, a guidewire torquer that constitutes multiple low peaks and multiple low valleys, as shown in FIGS. 4A and B, will result in a sufficiently large friction for exerting a torque as required in use, without exceeding the maximum elastic deformability of stainless steel and consequently without deforming the stainless steel guidewire.

Figure 2C:
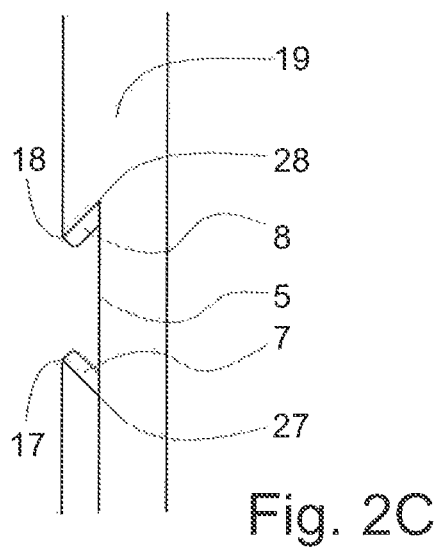
Figure 2D:
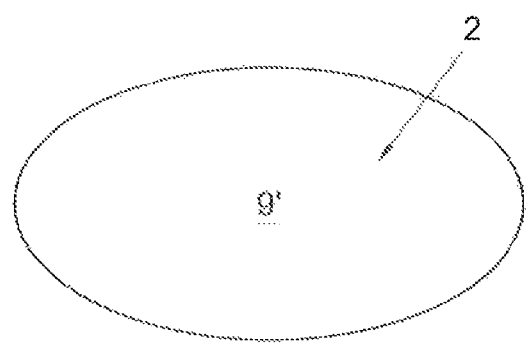

The guidewire holding surfaces 7, 8 and the abutment surface 5 are shown in greater detail in FIG. 2C. The abutment surface 5 of the insertion channel is bounded by guidewire holding surfaces 7, 8. The abutment surface 5 is connected with the guidewire holding surfaces 7, 8 via the angular transitions 27, 28. The guidewire holding surfaces 7, 8 extend to free edges 17, 18. Since the guidewire holding surfaces 7, 8 lean over towards a plane defined by the abutment surface 5, the guidewire holding surfaces 7, 8 urge the guidewire towards the abutment surface 5 as a result of the urging force of the guidewire which is inclined to self straighten.

For holding the guidewire particularly reliably against or near the abutment plane, preferably at least two of the guidewire holding surfaces lean over obliquely towards the abutment surface at an angle of more than 25° and more preferably more than 30° or more than 35° (each relative to a direction perpendicular to the abutment plane).

For the purpose of operation, the guidewire 3 is arranged against the abutment surface 5 while flexing it past the guidewire holding surfaces 7, 8. Subsequently, the physician is able to control the rotational orientation of the guidewire 3 and a tip at the distal end thereof. Thus, the physician is able to steer and to navigate the guidewire through a duct of a patient, such as a vasculature or a hollow organ (e.g. the urinary tract, the gastro-intestinal tract or the bile ducts) of the patient. The physician is also able to both easily mount the guidewire torquer to the guidewire and to easily unlock the torquer from the guidewire. Therefore, the user is able to quickly move the guidewire torquer from the one to the other location on the guidewire. These features are particularly useful by saving time for performing a procedure.

Figure 3A:
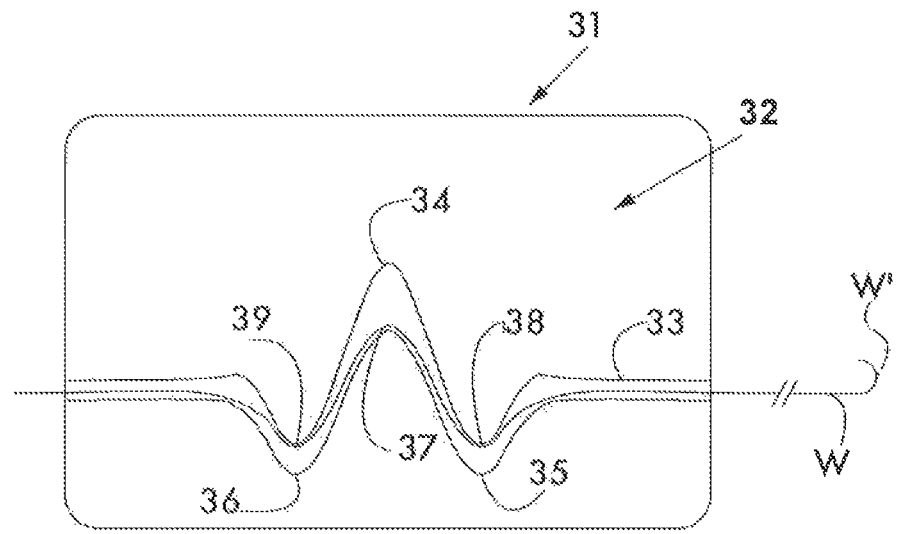
FIGS. 3A, 3B, 3C and 3D provide a further preferred embodiment according to the present invention being mounted on a guidewire.

FIG. 3A shows a front view of a guidewire torquer 31. The guidewire torquer 31 is comprised of a handling body 32 and an insertion channel 33 constituted by guidewire holding surfaces and an abutment surface forming the bottom of the insertion channel. Also, a guidewire W with a tip W' at its distal end is shown, resting in the insertion channel. The insertion channel 33 has a wavy or sinusoid shape having one top bend 34 and two bottom bends 35 and 36. Due to its natural stiffness the guidewire reaches the position in which the guidewire W firmly touches the inner apexes 37, 38 and 39 of the bends in the insertion channel 33.

Due to the resulting friction between the guidewire W and the guidewire torquer 31 the guidewire substantially becomes functionally united with the guidewire torquer. The insertion channel 33 has an open side that is open to the side of the surface in which the channel is arranged. Because the open side of the insertion channel 33 is narrower than a largest width of the channel, the guidewire W is reliably prevented from flipping out of the channel.

Figure 3B:
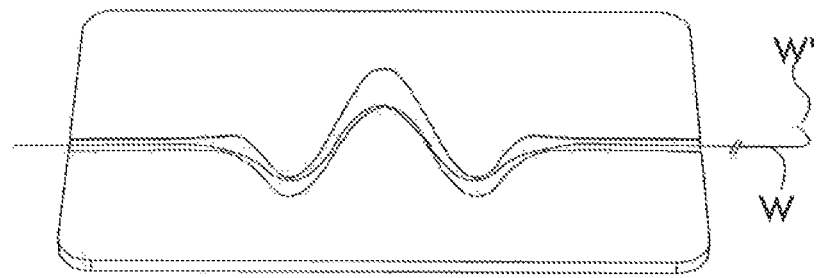
Figure 3C:
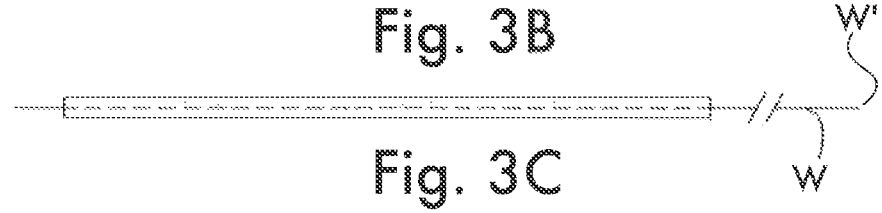
Figure 3D:
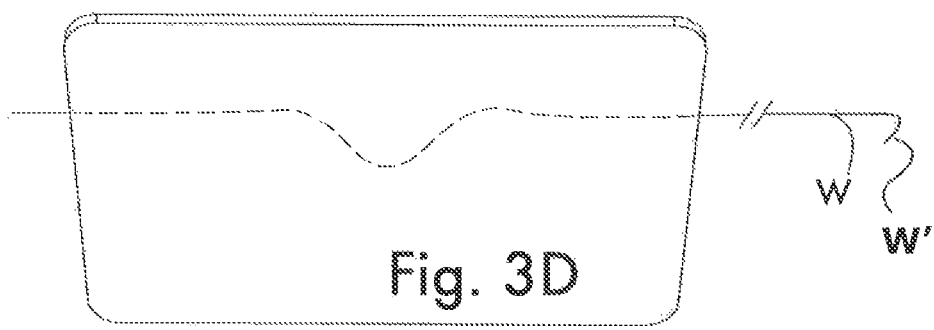

Therefore, as is illustrated in the FIGS. 3B, 3C and 3D, the rotational orientation of the guidewire in the insertion channel is precisely defined by the rotational orientation of the guidewire torquer.

Compared to FIG. 3A, the guidewire torquer 31 has been tilted 45 degrees backwards in FIG. 3B, resulting concurrently in a similar change in rotational orientation of the distal tip W' backwards over 45 degrees. Likewise, in the FIGS. 3C and 3D a backwards tilt of the guidewire torquer over 90 and 135 degrees directly causes a corresponding backwards rotation of the distal tip W' over 90 and 135 degrees.

Therefore, the guidewire torquer continuously gives precise visible and tactile feedback to the physician about the actual rotational orientation of the tip of the guidewire inside the body of the patient.

FIG. 4A shows a further preferred embodiment of a guidewire torquer 41 with a substantially flat handling body 42 in a shape having a convex right side 43 and a left side with 2 recesses 44, 45 and a protrusion 46 in between. An insertion channel 47 with multiple low amplitude bends extends from the protrusion 46 to the convex right side 43 of this embodiment. The top side 48 and the bottom side 49 of the guidewire torquer 41 are symmetrically and widely spaced from the insertion channel 47. FIG. 4B shows the guidewire torquer 41 mounted on a guidewire W whose distal tip W' has a curved shape.

Functionally, the configuration of this embodiment provides the guidewire torquer 41 with a stable position when positioned on a flat surface. A rotational force exerted to the guidewire torquer, transmitted to the torquer e.g. by the guidewire W, will not result in rotation of the guidewire torquer. Therefore, withstanding the exerted rotational force, the guidewire torquer 41 will remain unchanged in its stable position relative to the flat surface it has been laid upon. As described in the above, when a guidewire torquer of the present invention is mounted on a guidewire, together they form one functional unit due to the firm fixation of the torquer relative to the guidewire. Therefore, the embodiment shown in FIG. 4, as well as other embodiments, serves as a stabilizer relative to the surface it is laid upon of the rotational orientation both of the guidewire torquer 41 and of the guidewire W.

Moreover, the purpose of this embodiment is to keep the tip W' of the guidewire reliably pointing to a specific desired direction during advancement of the guidewire in the human body. In FIG. 4B the tip W' is directed into the same direction as the bottom side 49 of the guidewire torquer 41, which direction is downwards. Due to its substantially flat shape the guidewire torquer 41 will remain in parallel position to the surface it is laid upon when it is dragged to the right over the surface by the guidewire, in a procedure where the physician advances the tip W' of the guidewire further into the human body.

An example of such procedure is a placement of a central vein catheter (CVC). The CVC is fed over the guidewire W which tip W' first has been navigated from the subclavian vein into the central vein. During the navigation of the guidewire to the central vein the guidewire torquer 41 keeps the tip W' of the guidewire constantly directed downwards, that is into the direction of the central vein. Consequently, the tip W' preferentially enters the central vein. So, the function of the guidewire torquer 41 is to allow for the correct placement of the guidewire W in the central vein, and therefore to allow for the correct placement of the CVC that is fed over it.

By doing so the guidewire torquer 41 prevents the tip W' of the guidewire to turn upwards and erroneously enter the jugular vein, resulting in the CVC erroneously being fed over the guidewire into the jugular vein as well. Such misplacement of the CVC is the most frequent complication of CVC placement procedures.

FIG. 5 provides a preferred embodiment in which a guidewire torquer 51 has a thicker top side 52 than a bottom side 53. This asymmetry provides the user tactile information as to the position of the top side 52 relatively to the position of the bottom side 53 of the guidewire torquer 51. The bottom side 53 has three indentations 54, 55 and 56, that allow for further improved tactile feedback as well as for a firm grip on the guidewire torquer by fingers of the physician when feeling the indentations or placed therein.

The guidewire torquer 51 has an insertion channel 57 that is substantially shaped like a U-turn. Therefore, a proximal portion WP of a guidewire W that has been inserted in the U-turn shaped insertion channel 57 points into the same direction as a distal portion WD of the guidewire W. The proximal portion WP has a proximal tip WP' with a shape that resembles the shape of the distal tip WD'.

A combination of the guidewire W and the guidewire torquer 51 provides the physician with information as to both the rotational orientation and the insertion depth of the distal end WD' of the guidewire the text the insertion depth of a guidewire measures a distance from a distal end of the guidewire located inside the human body to a point of entry of the guidewire into the patient. In FIG. 5 the insertion depth of the guidewire W measures the distance 58 between the distal end WD' and the point of entry 59 of the guidewire into the human body. Without any measurement, the insertion depth of the guidewire W is visually indicated by the position of the proximal tip WP', whenever the guidewire has been positioned in the insertion channel 57 in a symmetrical way relatively to the U-turn curve, which is the case in FIG. 5.

Using the guidewire torquer 51 can be highly advantageous because it allows the physician to substantially reduce screening time and therefore the procedural radiation exposure. Indeed, visible and tactile feedback that is provided by the guidewire torquer 51 about the rotational orientation and the insertion depth of the guidewire is available for the physician without the need for additional fluoroscopy.

Obtaining such information without the said feedback inevitably requires screening of the guidewire inside the patient, thereby increasing the amount of radiation exposure and prolonging the procedure time. In contrast, the rotational orientation and the insertion depth of the distal tip of the guidewire inside the human body can be easily and continuously derived from the rotational orientation and position of the proximal tip that is readily visible outside the human body.

Figure 6:
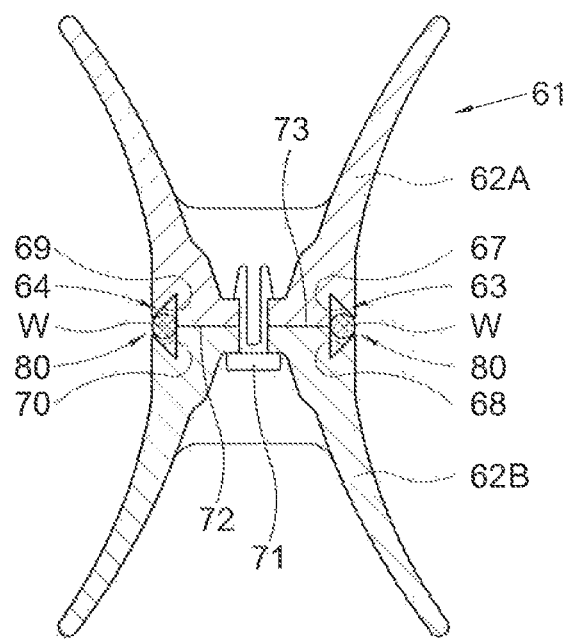
FIG. 6 provides a front cross-sectional view of a further preferred embodiment according to the present invention.
Figure 7:
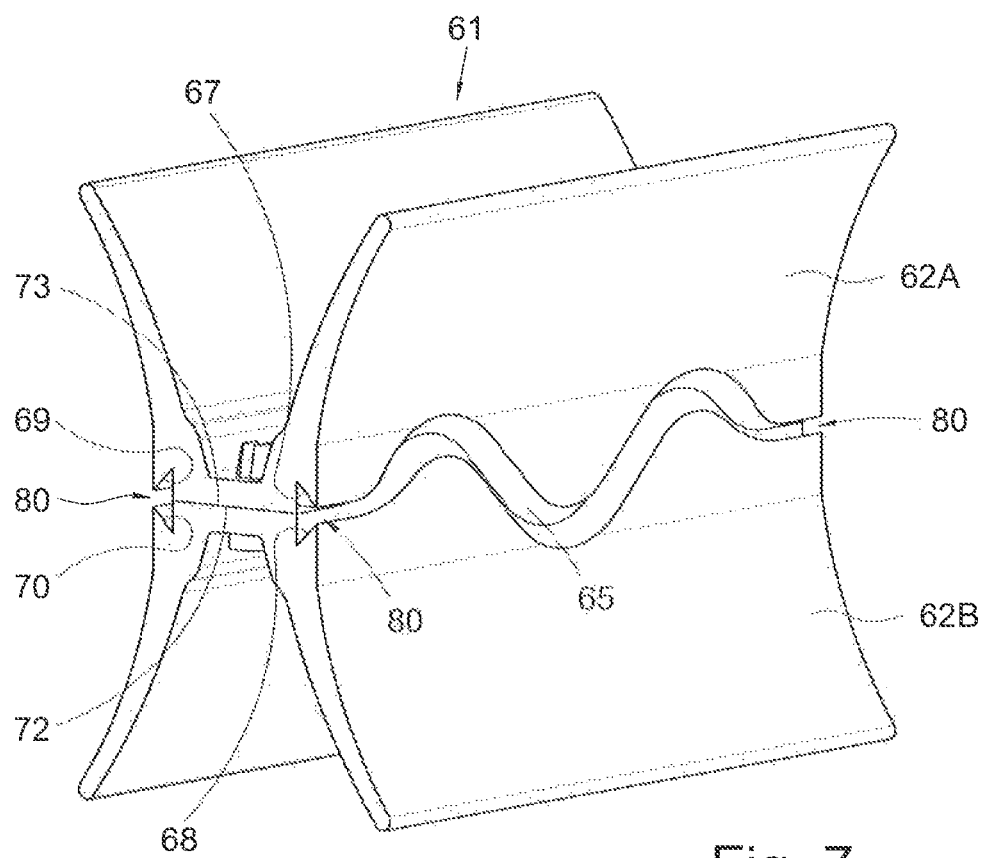
FIG. 7 provides a perspective view of the embodiment shown in FIG. 6.

In FIGS. 6 and 7, an embodiment of a torquer 61 according to the invention is shown, which is provided with two groups of guidewire holding surfaces 67, 68 and 69, 70. These groups of guidewire holding surfaces 67, 68 and 69, 70 are arranged for holding guidewires ire mutually different curved shapes and for holding guidewires on mutually opposite sides of the guidewire torquer 61, so that the guidewire holding surfaces of one group does not interfere with the guidewire holding surfaces of a group on the other side and a great freedom of design regarding the curvature imposed can be obtained in a compact torquer design.

In particular, guidewire holding surfaces for holding a Nitinol guidewire is preferably shaped for bolding the guidewire in a configuration curved with a smaller radius of curvature than guidewire holding surfaces for holding a stainless steel guidewire of the same thickness, since the smallest radius of curvature to which stainless steel can be bent without causing permanent deformation is larger than the smallest radius of curvature to which Nitinol of the same thickness can be bent without causing permanent deformation.

Guidewire holding surfaces for holding a stainless steel guidewire are preferably shaped for holding the guidewire in a shape including a larger number of bends (e.g. three, four or more sinusoids) than guidewire holding surfaces for holding a Nitinol guidewire, to ensure that at a smaller degree of deformation enough normal force is exerted onto the guidewire to cause enough friction for preventing the guidewire from rotationally slipping in the torquer during an intervention. On the other hand, holding the guidewire in a configuration with a smaller number of curves, (e.g. one, two or three sinusoids) is advantageous because engaging a relatively short section of the guidewire can be sufficient. Consequently, the length of the insertion channel can be shorter and the size of the guidewire torquer in generally longitudinal direction of the guidewire can be smaller.

In this embodiment a body of the torquer 61 consists of two body halves 62A and 62B mounted to each other along curved and mutually matching surfaces 72, 73 that end in bottoms 65 of insertion channels 63, 64 each further bounded by one of the guidewire holding surface groups 67, 68 and 69, 70. In spite of the guidewire bolding surfaces 67, 68 and 69, 70 of each of the insertion channels 63, 64 being further apart at the bottom of the insertion channel than at the top of the respective insertion channel, the torquer body halves 62A and 62B can be made by injection molding and are attached to each other by fasteners 71, but other forms of attachment are also conceivable.

The guidewire holding surface groups 67, 68 and 69, 70 form narrowed passages 80 at the open side of the insertion channel 63, 64 that are each slightly narrower than the diameter of the guidewire W and of a stiffness allowing a guidewire W to be snapped through the passages 80 into a position between the guidewire holding surfaces 67, 68 and 69, 70. Thus, a particularly reliable connection of the torquer 61 to the guidewire W achieved. A particular advantage is that the snapping effect provides tactile feedback ensuring reliable engagement of the torquer 61 to the guidewire W even if the guidewire is inserted without looking at the torquer and the section of the guidewire W that is inserted, e.g. while watching a fluoroscopic display showing the guidewire tip for holding the tip of the guidewire stationary inside a patient.

Because the narrowed passages 80 are located at outer ends of the torquer 61 a particularly reliable engagement of the guidewire W in the torquer 61 is obtained, so that even exertion of some bending force causing the guidewire to be pushed to the open side of the passage 80 does not lead to dislodgement of the guidewire W from the torquer 61.

Figure 8:
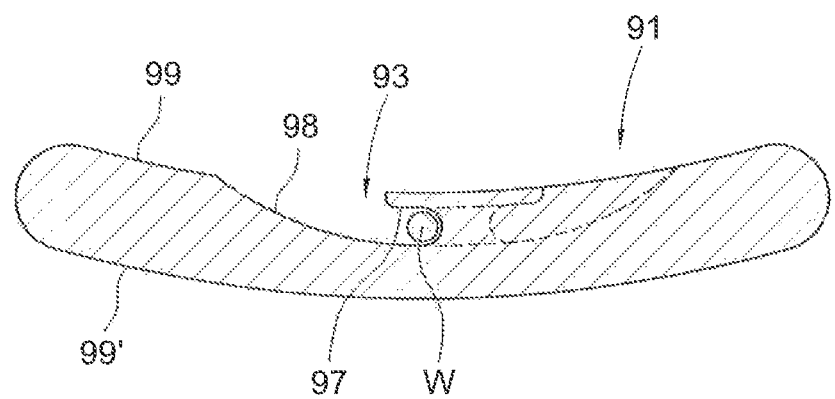
FIG. 8 provides a front cross-sectional view of a further preferred embodiment according to the present invention along the line VIII-VIII in FIG. 9.
Figure 9:
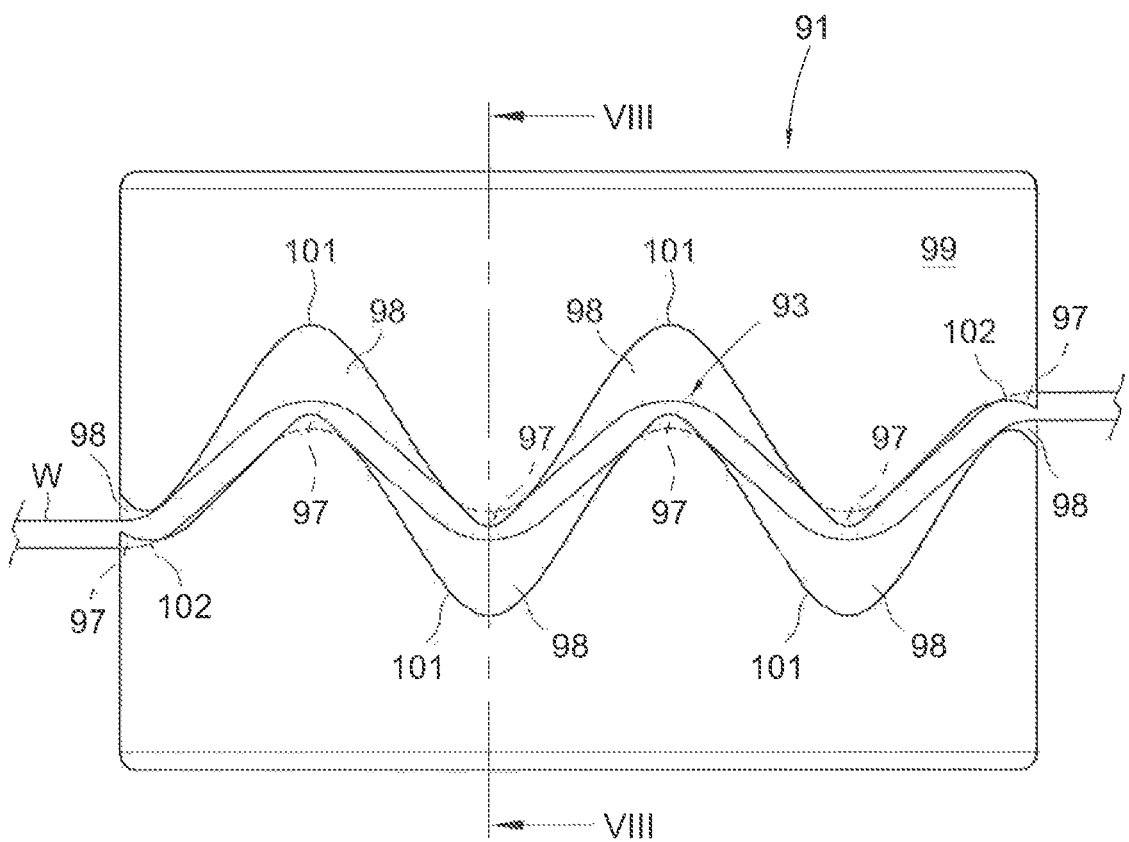
FIG. 9 provides a side view of the torquer and guidewire shown in FIG. 8.

FIGS. 8 and 9 show an embodiment 91 in which a handling body has a hollow surface 99 and a bellied surface 99'. In this example, the hollow surface 99 is provided with an insertion channel 93. Providing the insertion channel 93 in a hollow surface 99 is advantageous for easy lateral insertion of a guidewire W into the insertion channel 93, because slipping away sideways of the guidewire W over the surface 99 of the handling body is counteracted. However, one or more insertion channels may also be provided in the bellied surface.

As is best seen in FIG. 8, abutment surfaces banning undercuts 97 in the insertion channel 93 may each be provided to one side only. The channel side wall surfaces 98 each on a side of the opposite of the undercut 97 in the same section of the channel 93 are sloping gradually from a surface to a side of the channel towards the undercut 97 and face an open side of the channel 93. This allows the guidewire W to be pushed into the channel particularly easily. The average sloping angle of the sloping channel side wall surfaces 98 is preferably less steep than 1:1, and more preferably less steep than 1:2 or 1:3. As is illustrated by FIG. 9, undercuts 97 are preferably provided in each bend 101, 102 at the side of the abutment surface that is contacted by the guidewire W due to the lateral force exerted thereto bending the guidewire W into a curved configuration, so that insertion of the guidewire W into the channel 93 and subsequent removal of the guidewire W from the channel 93 can be carried out easily. The present invention is described in the foregoing on the basis of several preferred embodiments. Different aspects of different embodiments can be combined, wherein all combinations which can be made by a skilled person on the basis of this document must be included. These preferred embodiments are not limitative for the scope of protection of this document. The rights sought are defined in the appended claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or inure of the listed items (A and B), unless otherwise indicated herein or clearly contradicted by context. The terms "comprising," "having," "including," and "containing" are to be construed as open-ended terms (i.e., meaning "including, hut not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventor for carrying out the invention. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A guidewire torquer for manually controlling a guidewire and imparting motion to a guidewire, the guidewire torquer comprising:
    a handling body for handling of the guidewire torquer; and
    guidewire holding surfaces oriented for engaging the guidewire from mutually opposite sides of the guidewire and holding the guidewire in an elastically tensioned, bent guidewire shape, the guidewire holding surfaces providing frictional fixation of the guidewire relative to the handling body in a position extending along a guidewire trajectory along and touching the guidewire holding surfaces,
    wherein the guidewire holding surfaces project from at least one abutment surface connected to the guidewire holding surfaces via angular transitions,
    wherein the guidewire trajectory is accessible from a direction in which the at least one abutment surface is facing,
    wherein at least two of the guidewire holding surfaces oriented for engaging the guidewire from mutually opposite sides of the guidewire lean over obliquely towards the abutment surface at an angle of more than 25°, and
    wherein the guidewire holding surfaces are part of a single, rigid body portion, at least the handling body being of a material having a modulus of elasticity of at least 0.5 GPa.

2. The guidewire torquer according to claim 1, further comprising at least two groups of guidewire holding surfaces, a first one of said groups being arranged for holding a first guidewire in a first curved shape, a second one of said groups being arranged for holding a second guidewire in a second curved shape, said second curved shape being different from said first curved shape, wherein said first group of guidewire holding surfaces is arranged for holding the first guidewire on a first side of the guidewire torquer and said second group of guidewire holding surfaces is arranged for holding the second guidewire on a second side of the guidewire torque, and said second side being opposite to said first side.

3. The guidewire torquer according to claim 1, wherein at least portions of the guidewire holding surfaces have a higher coefficient of friction relative to a guidewire than other surface portions of the torquer.

4. The guidewire torquer according to claim 1, in which the guidewire holding surfaces form a curved insertion channel in the handling body, and in which the insertion channel is open on one side, wherein the insertion channel has at least one portion in which, seen in cross-section, the open side of the insertion channel is narrower than a largest width of the insertion channel.

5. The guidewire torquer according to claim 1, wherein at least two of the guidewire holding surfaces lean over obliquely towards the abutment surface at an angle of more than 30°.

6. The guidewire torquer according to claim 1, of a material having a modulus of elasticity of at least 1.0 GPa.

7. The guidewire torquer according to claim 1, having a material thickness at the abutment surface of at least 2 mm.

8. The guidewire torquer according to claim 1, wherein the guidewire holding surfaces are arranged such that said bent guidewire shape includes a succession of bends that are curved in a common plane, in a view perpendicular to the common plane, and
   wherein the succession of bends has an amplitude of more than 0.1 times a distance between successive peaks or between successive deepest positions of valleys in the succession of bends.

9. The guidewire torquer according to claim 8, wherein the guidewire holding surfaces are arranged such that, in a view of said bent guidewire shape perpendicular to a plane in which the guidewire is curved, the succession of bends constitutes at least two peaks or at least two valleys.

10. A kit comprising:
   a guidewire, and
   a guidewire torquer for manually controlling a guidewire and imparting motion to a guidewire, the guidewire torquer comprising:
      a handling body for handling of the guidewire torquer; and
      guidewire holding surfaces oriented for engaging the guidewire from mutually opposite sides of the guidewire and holding the guidewire in an elastically tensioned, bent guidewire shape providing frictional fixation of the guidewire relative to the handling body in a position extending along a guidewire trajectory along and touching the guidewire holding surfaces,
   wherein the guidewire holding surfaces project from at least one abutment surface against which the guidewire abuts when held in said elastically tensioned, bent guidewire shape, said abutment surface being connected to the guidewire holding surfaces via angular transitions,
   wherein the guidewire trajectory is accessible from a direction in which the at least one abutment surface is facing,
   wherein at least two of the guidewire holding surfaces oriented for engaging the guidewire from mutually opposite sides of the guidewire lean over obliquely towards the abutment surface at an angle of more than 25°, and
   wherein the guidewire holding surfaces are part of a single, rigid body portion, at least the handling body being of a material having a modulus of elasticity of at least 0.5 GPa.

11. The guidewire torquer according to claim 1, wherein at least two of the guidewire holding surfaces lean over obliquely towards the abutment surface at an angle of more than 35°.

12. The guidewire torquer according to claim 1, of a material having a modulus of elasticity of at least 1.5 GPa.

13. The guidewire torquer according to claim 1, having a material thickness at the abutment surface of at least 3 mm.

14. The guidewire torquer according to claim 1, wherein the guidewire holding surfaces are arranged such that said bent guidewire shape includes a succession of bends that are curved in a common plane, in a view perpendicular to the common plane, and
   wherein the succession of bends has an amplitude of more than 0.2 times a distance between successive peaks or between successive deepest positions of valleys in the succession of bends.

\* \* \* \* \*